(12) United States Patent
Ide et al.

(10) Patent No.: US 8,313,702 B2
(45) Date of Patent: Nov. 20, 2012

(54) GEL MANUFACTURING APPARATUS

(75) Inventors: Katsuya Ide, Suwa (JP); Kei Hiruma, Chino (JP)

(73) Assignee: Seiko Epson Corporation, Tokyo (JP)

( * ) Notice: Subject to any disclaimer, the term of this patent is extended or adjusted under 35 U.S.C. 154(b) by 329 days.

(21) Appl. No.: 12/827,106

(22) Filed: Jun. 30, 2010

(65) Prior Publication Data

US 2011/0014089 A1    Jan. 20, 2011

(30) Foreign Application Priority Data

Jul. 16, 2009   (JP) ................. 2009-167542

(51) Int. Cl.
*A61K 9/48*   (2006.01)
*A61K 9/50*   (2006.01)
*A61J 3/07*   (2006.01)

(52) U.S. Cl. ............ 422/129; 422/128; 422/106; 425/5; 264/4; 264/4.1; 264/4.3

(58) Field of Classification Search ............... 422/106, 422/128, 129; 424/451, 456, 463; 425/5; 264/4, 4.1, 4.3

See application file for complete search history.

(56) References Cited

U.S. PATENT DOCUMENTS

| | | | | |
|---|---|---|---|---|
| 3,015,128 A | * | 1/1962 | Somerville, Jr. | 425/5 |
| 4,344,787 A | * | 8/1982 | Beggs et al. | 65/21.4 |
| 4,692,284 A | * | 9/1987 | Braden | 264/4.3 |
| 5,462,866 A | * | 10/1995 | Wang | 435/174 |
| 6,377,387 B1 | * | 4/2002 | Duthaler et al. | 359/296 |
| 7,578,951 B2 | * | 8/2009 | Dunfield et al. | 264/4.1 |

FOREIGN PATENT DOCUMENTS

| | | |
|---|---|---|
| JP | 29-002449 | 5/1954 |
| JP | 56-117762 | 9/1981 |
| JP | 03-043320 U | 4/1991 |
| JP | 2001-232178 | 8/2001 |
| JP | 2004-300426 | 10/2004 |
| JP | 2005-211898 | 8/2005 |
| JP | 2007-245151 | 9/2007 |

* cited by examiner

*Primary Examiner* — Walter D Griffin
*Assistant Examiner* — Huy-Tram Nguyen
(74) *Attorney, Agent, or Firm* — Maschoff Gilmore & Israelsen

(57) ABSTRACT

A gel manufacturing apparatus adapted to generate gel by making a first solution and a second solution react with each other includes: a flow mechanism adapted to make the second solution flow; an ejection mechanism having a nozzle plate provided with a nozzle adapted to eject the first solution to the second solution made to flow using a droplet ejection method; and a gap plate provided with a through hole communicated with the nozzle, wherein the gap plate is disposed between the flow mechanism and the ejection mechanism.

13 Claims, 7 Drawing Sheets

GEL MANUFACTURING APPARATUS

BACKGROUND

1. Technical Field

The present invention relates to a gel manufacturing apparatus.

2. Related Art

As a related art technology, there is known a method of manufacturing gel by ejecting an ejection liquid using a droplet ejection method toward an ejection target liquid. For example, there is disclosed a method and an apparatus of disposing an ejection port (a nozzle) for ejecting an ejection substance so as to face an ejection target liquid in a resting state with a predetermined distance therefrom, and making the ejection substance ejected from the nozzle using the droplet ejection method and the ejection target liquid in the resting state react with each other, thereby manufacturing gel (see, e.g., JP-A-2001-232178).

Further, there is disclosed a method of disposing the ejection port (the nozzle) so as to have contact with a surface of the ejection target liquid, and ejecting the ejection liquid toward the ejection target liquid using the droplet ejection method, thereby manufacturing gel (see, e.g., JP-A-2007-245151).

However, since the distance (interval) between an inkjet head and the surface of the ejection target liquid is as close as 0.1 mm through 1 cm, there arises a problem that the surface of the ejection target liquid waves due to a vibration caused by the ejection substance ejected to the surface of the ejection target liquid, and the ejection target liquid enters inside the nozzle of the inkjet head to make the ejection substance and the ejection target liquid react with each other inside the nozzle to thereby generate the gel, which incurs an ejection failure.

SUMMARY

An advantage of some aspects of the invention is to solve at least a part of the problem described above, and the invention can be realized as the following embodiments or aspects of the invention.

According to a first aspect of the invention, there is provided a gel manufacturing apparatus adapted to generate gel by making a first solution and a second solution react with each other including a flow mechanism adapted to make the second solution flow, an ejection mechanism having a nozzle plate provided with a nozzle adapted to eject the first solution to the second solution made to flow using a droplet ejection method, and a gap plate provided with a through hole communicated with the nozzle, wherein the gap plate is disposed between the flow mechanism and the ejection mechanism.

According to this configuration, since the distance (interval) between the nozzle of the ejection mechanism and the second solution flowing trough the flow section of the flow mechanism is controlled by a thickness (the thickness of the gap plate in the direction in which the first solution is ejected) of the gap plate, it becomes easy to control the distance (interval). Further, since the second solution is prevented from getting into the nozzle of the ejection mechanism via the through hole of the gap plate due to the wave of the liquid surface of the second solution caused by the flow of the second solution, and at the same time, the wave of the liquid surface is also suppressed, it is possible to prevent the nozzle of the ejection mechanism from choking with the second solution. Thus, since it is possible to stably eject the first solution from the nozzle of the ejection mechanism toward the second solution flowing through the flow section of the flow mechanism using the droplet ejection method, it becomes possible to stably obtain the gel generated from the first solution and the second solution reacting chemically with each other.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

A first embodiment of the invention will hereinafter be explained with reference to FIGS. 1 through 3.

Figure 1:
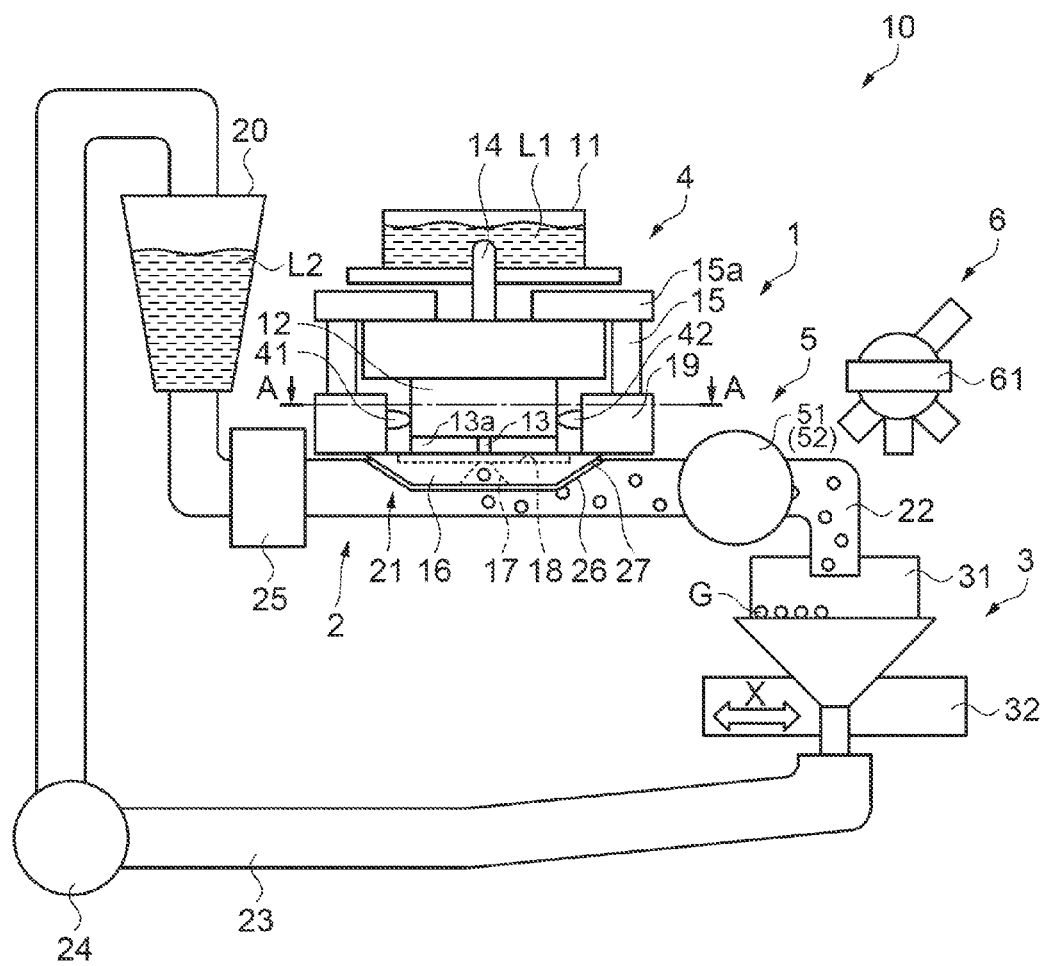
FIG. 1 is a schematic side view showing a gel manufacturing apparatus according to a first embodiment.
Figure 2:
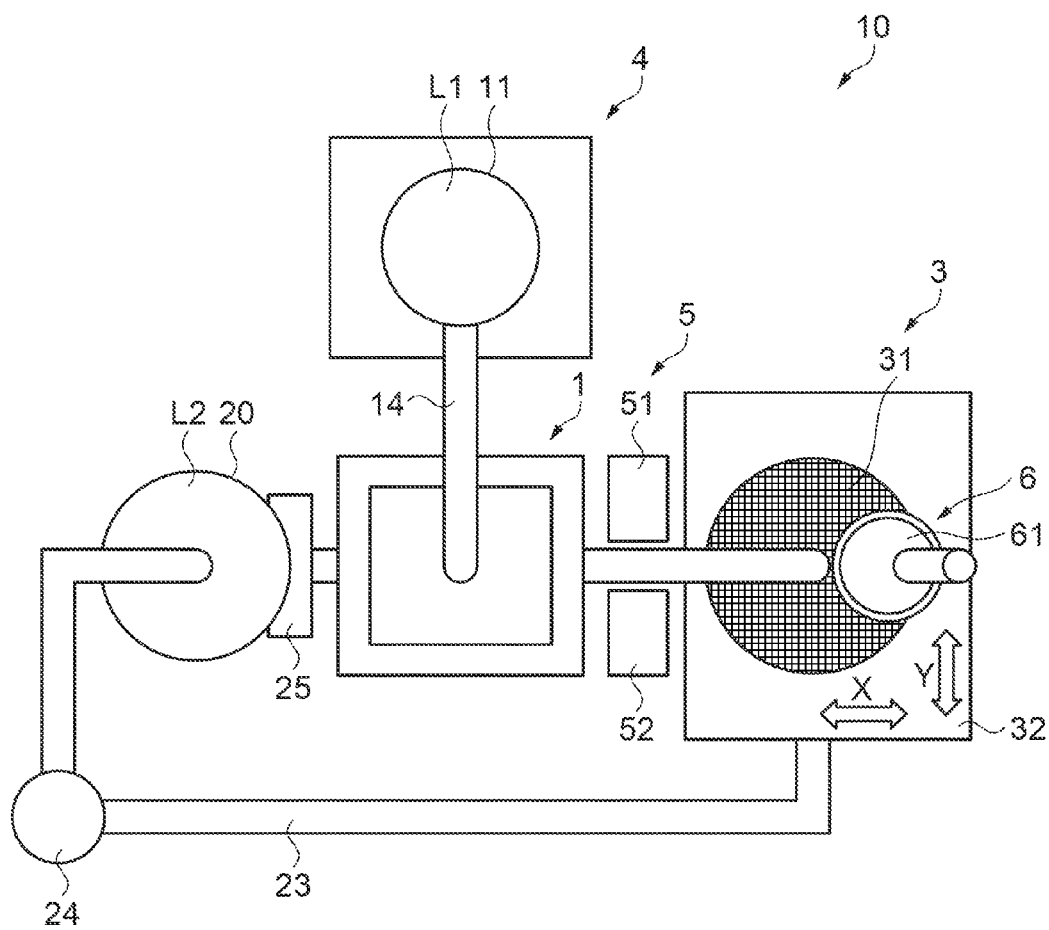
FIG. 2 is a schematic plan view showing the gel manufacturing apparatus according to the first embodiment.

As shown in FIGS. 1 and 2, the gel manufacturing apparatus 10 according to the first embodiment is provided with an ejection mechanism 1, a flow mechanism 2, a gel collection mechanism 3, an ejection measurement mechanism 4, a gel weighing mechanism 5, and an observation mechanism 6.

The gel manufacturing apparatus 10 ejects a first solution L1 from the ejection mechanism 1 toward a second solution L2 flowing through the flow mechanism 2 using the droplet ejection method, thereby obtaining the gel G generated from the first solution L1 and the second solution L2 reacting chemically in a discharge section 22. Specifically, sodium alginate water solution is used as the first solution L1, and calcium chloride water solution is used as the second solution L2. By ejecting the sodium alginate water solution toward the calcium chloride water solution, sodium alginate and calcium chloride react chemically with each other to generate the calcium alginate gel.

The ejection mechanism 1 ejects the first solution L1 using the droplet ejection method.

The ejection mechanism 1 is provided with a first reservoir 11 for containing the first solution L1, an inkjet head 12, a supply pipe 14 for supplying the first solution L1 from the first reservoir 11 to the inkjet head 12, a gap plate 16, a reinforcing plate 19, fixing columns 15, and fixing jigs 15a.

The inkjet head 12 has a nozzle plate 13a provided with a nozzle 13. It is assumed that the nozzle 13 has a diameter of, for example, 100 μm, and the first solution L1 ejected from the nozzle 13 at an ejection frequency of no lower than 10 Hz has a flow rate of 1 mm/s. Although according to the drawings a single nozzle 13 is formed, this is not a limitation, but it is also possible to form two or more nozzles 13. Further, although a single inkjet head 12 is provided to the ejection mechanism 1 according to the drawings, this is not a limitation, but a configuration of providing two or more inkjet heads 12 to the ejection mechanism 1 can also be adopted.

The gap plate 16 is provided with a through hole 17 and a groove 18. The gap plate 16 is made, for example, of transparent acrylic resin. By using the transparent gap plate 16, the alignment between the nozzle 13 and the through hole 17 can easily be performed while checking it visually using a microscope and so on. The through hole 17 and the nozzle 13 are arranged so as to form a continuous hole. Thus, there is provided a configuration that the first solution L1 ejected from the nozzle 13 passes through the through hole 17. The through hole 17 is provided with a water-repellent coating such as fluorine series or silicon series. Similarly, the gap plate 16 is provided with a water-repellent coating such as fluorine series or silicon series. It is assumed that the diameter of the through hole 17 on the side facing the nozzle 13 is equivalent to or larger than the diameter of the nozzle 13. Further, it is also assumed that the diameter of the through hole on the other side is equivalent to or larger than the diameter of the through hole 17 on the side facing the nozzle 13. In other words, the through hole 17 has a cylindrical shape with a constant diameter or a tapered shape with a diameter increasing in a direction from the side facing the nozzle 13 to the other side. The angle of the tapered shape can arbitrarily determined within a range from 90 degrees to 180 degrees. Further, a flow section 21 side of the through hole 17 is worked to have a round shape.

The gap plate 16 is fixed to the reinforcing plate 19 formed like a frame with an adhesive or the like. The mechanical strength of the gap plate 16 is reinforced by the reinforcing plate 19. The outer shapes of the gap plate 16 and the reinforcing plate 19 are formed so as to be thinner from the reinforcing plate 19 to the gap plate 16.

Figure 3:
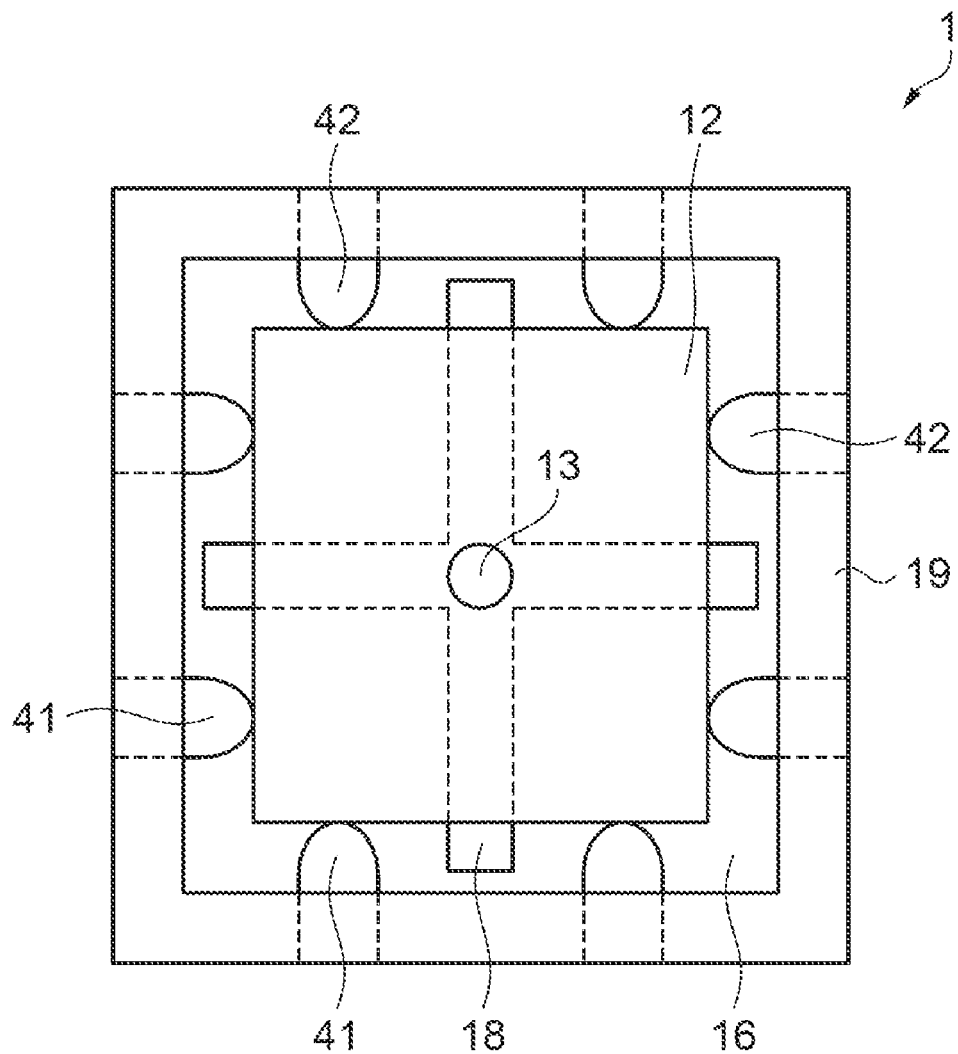
FIG. 3 is a cross-sectional view along the line A-A shown in FIG. 1.

Further, as shown in FIG. 3, the inkjet head 12 is disposed inside the frame of the reinforcing plate 19. The inkjet head 12 is fixed by positioning pins 41 and spring pins 42 disposed on the two sides of the reinforcing plate 19 each having a frame shape and opposed to each other, while the nozzle 13 and the through hole 17 are aligned to each other. The reinforcing plate 19 is provided with, for example, four fixing columns 15. Further, using the fixing jigs 15a attached to the tips of the respective fixing columns 15, the inkjet head 12 is fixed to the gap plate 16. Further, the inkjet head 12 can detachably attached to the gap plate 16 due to the fixing jigs 15a.

The groove 18 is provided to the gap plate 16 on the side of the inkjet head 12 (on the surface opposed to the inkjet head). Further, the groove is formed so as to be connected to the through hole 17 and to extend in four directions shown in FIG. 3, for example. In the condition in which the inkjet head 12 overlaps the gap plate 16, the groove 18 of the gap plate 16 is not entirely shielded by the inkjet head 12, but is exposed therefrom at least partially. Further, the depth of the groove 18 is about a half of the thickness of the gap plate 16. The groove 18 is provided with a water-repellent coating of fluorine series.

The flow mechanism 2 makes the second solution L2 flow. Further, the flow mechanism 2 circulates the second solution L2.

The flow mechanism 2 is provided with a second reservoir 20 for containing the second solution L2, the flow section 21 and the discharge section 22 through which the second solution L2 flows, and a solution circulation section 23. The second reservoir 20 is communicated with a filter 25 and the flow section 21. The discharge section 22 is communicated with the flow section 21. The second solution L2 contained in the second reservoir 20 is filtrated by the filter 25, and fed to the flow section 21 and the discharge section 22. Further, the discharge section 22 transmits the second solution L2 having flown through the flow section 21 and the gel G thus generated. The solution circulation section 23 is provided with, for example, a pump 24. The second solution L2 having passed through the discharge section 22 is collected by the solution circulation section 23, and then circulated by the pump 24 to the second reservoir 20.

The flow section 21 is provided with a head mount section 26. For example, as shown in the drawing, the head mount section 26 is obtained by cutting a part of the flow section 21 so as to follow the shapes of the gap plate 16 and the reinforcing plate 19 to thereby expose the inside of the tubular shape of the flow section 21. Here, as shown in the drawings, since the structure from the reinforcing plate 19 to the gap plate 16 is formed so as to be thinner, in the head mount section 26, the inside of the tubular shape of the flow section 21 is formed to be thinner compared to the outside of the tubular shape thereof. Further, it is also possible to dispose a valve between the second reservoir 20 and the filter 25, or between the filter 25 and the head mount section 26 of the flow section 21 to control the flow volume or the flow velocity of the flow to the flow section 21.

The second reservoir 20 is made of, for example, transparent or translucent polyethylene. The flow section 21 and the discharge section 22 are made of, for example, transparent acrylic resin, and are each formed to have a tubular shape. The discharge section 22 is formed to have an L shape, and is arranged so that the second solution L2 flowing from the flow section 21 does not fly in all directions from the discharge section 22.

The head mount section 26 is provided with a seal section 27 such as waterproof rubber or an O-ring. Further, the gap plate 16 and the reinforcing plate 19 of the ejection mechanism 1 are disposed on the head mount section 26, and are sealed by the seal section 27 so that the second solution L2 flowing through the flow section 21 does not flow out of the flow section 21. Further, the seal section 27 can be fixed to the gap plate 16 and the reinforcing plate 19 of the ejection mechanism 1 with an adhesive.

Since negative pressure is caused inside the through hole 17 of the gap plate 16 when the second solution L2 flows between the flow section 21 and the gap plate 16, flow of the air (gas) from the groove 18 to the through hole 17 is caused by making the most use of this phenomenon. Thus, it is possible to prevent the second solution L2 from flowing from the flow mechanism 2 into the through hole 17 of the gap plate 16. Further, it is also possible to maintain or help the ejection velocity of the first solution L1 ejected from the nozzle 13 of the inkjet head 12.

Further, since the flow section 21 side of the through hole 17 is worked to have a round shape in the ejection mechanism 1, it is prevented that the second solution L2 flows from the through hole 17 of the gap plate 16 into the nozzle 13 of the inkjet head 12, and the nozzle 13 is prevented from choking with the second solution L2.

In order for defining the distance (interval) between the nozzle 13 of the inkjet head 12 and the surface of the second solution L2 made to flow by the flow mechanism 2, the thickness of the gap plate 16 is determined. In the present embodiment, the thickness is arbitrarily determined within a range no smaller than 0.1 mm, and no larger than 10 mm.

The solution circulation section 23 collects the second solution L2 having flown through the flow section 21, the discharge section 22, and a gel collection mechanism 3 described later, and circulate it to the second reservoir 20.

The gel collection mechanism 3 collects the gel G generated by ejecting the first solution L1 to the second solution L2 made to flow.

The gel collection mechanism 3 is provided with a collection net 31 and an XY table 32. The collection net 31 is disposed on the XY table 32. The collection net 31 is moved by moving the XY table 32 so that the gel G passing through the discharge section 22 of the flow mechanism 2 does not overlap with each other on the collection net 31. The mesh size of the collection net 31 is set to be no larger than the diameter 100 μm of the gel G, and specifically no larger than 80 μm, for example. Further, the moving speed of the XY table 32 is set to be no lower than 1 mm/s, in the case, for example, in which the diameter of the gel G is 100 μm, and the ejection frequency is 10 Hz.

The ejection measurement mechanism 4 measures the weight of the first reservoir 11 of the ejection mechanism 1. By measuring the weight of the first reservoir 11 for containing the first solution L1, the weight of the first solution L1 ejected from the nozzle 13 is measured using the difference in weight between before and after the ejection.

The gel weighing mechanism 5 is provided with a laser source 51 and a photoelectrical detector 52. The projection light projected from the laser source 51 is applied to the flow section 21 through which the second solution L2 and the gel G flow. Further, in the flow section 21, by receiving the reflected light, which is obtained by reflecting the projection light, by the photoelectrical detector 52, the number, the shape, and the size of the gel G thus generated are measured.

The observation mechanism 6 observes or measures the condition of the gel G collected by the gel collection mechanism 3, such as a shape or a size.

The observation mechanism 6 is provided with a camera 61. By shooting the gel G captured by the collection net 31 using the camera 61, the condition of the gel G thus generated, such as a shape or a size is observed or measured.

Therefore, according to the present embodiment, since the distance (interval) between the nozzle 13 of the inkjet head 12 and the second solution L2 flowing through the flow section 21 of the flow mechanism 2 is controlled by the thickness of the gap plate 16, the control of the distance (interval) becomes easy. Further, since the second solution L2 is prevented from getting into the nozzle 13 of the inkjet head 12 via the through hole 17 of the gap plate 16 due to the wave of the liquid surface of the second solution L2 caused by the flow of the second solution L2, and at the same time, the wave of the liquid surface is also suppressed, it is possible to prevent the nozzle 13 of the inkjet head 12 from choking with the second solution L2. Thus, since it is possible to stably eject the first solution L1 from the nozzle 13 of the inkjet head 12 toward the second solution L2 flowing through the flow section of the flow mechanism 2 using the droplet ejection method, it becomes possible to stably obtain the gel G generated from the first solution L1 and the second solution L2 reacting chemically with each other.

Further, since the second solution L2 flows through the flow section 21, the gel G generated from the first solution L1 and the second solution L2 reacting with each other can be prevented from overlapping with each other, and the gel G can be obtained individually even if the first solution L1 is continuously ejected by the inkjet head 12 toward the second solution L2.

Further, since the second solution L2 flows through the flow mechanism 2 without resting, it is possible to avoid the problems that the second solution L2 is contaminated or that living microbes are developed in the second solution L2.

Further, since the flow section 21 side of the through hole 17 is worked to have a round shape in the ejection mechanism 1, it is prevented that the second solution L2 flows from the through hole 17 of the gap plate 16 into the nozzle 13 of the inkjet head 12, and the nozzle 13 is prevented from choking with the second solution L2.

Second Embodiment

A second embodiment of the invention will hereinafter be explained with reference to FIGS. 4A, 4B, and 5.

In the gel manufacturing apparatus 10 according to the second embodiment, the constituents identical to those of the first embodiment shown in FIGS. 1 through 3 are denoted by the same reference numerals, and the explanations of the constituents will be omitted.

The gel manufacturing apparatus 10 according to the second embodiment is different from the gel manufacturing apparatus 10 according to the first embodiment in that a meandering section 28 is disposed between the head mount section 26 and the discharge section 22 of the flow section 21, and the meandering section 28 is provided with a warming section 29.

Figure 4A:
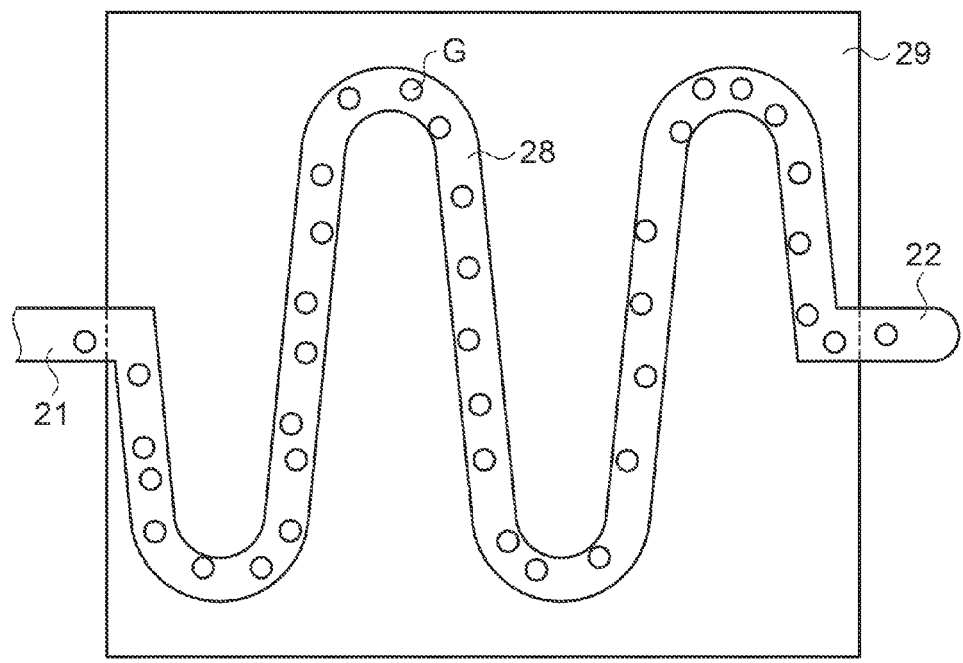
FIGS. 4A and 4B are schematic configuration diagrams showing a meandering section of a gel manufacturing apparatus according to a second embodiment.
Figure 4B:
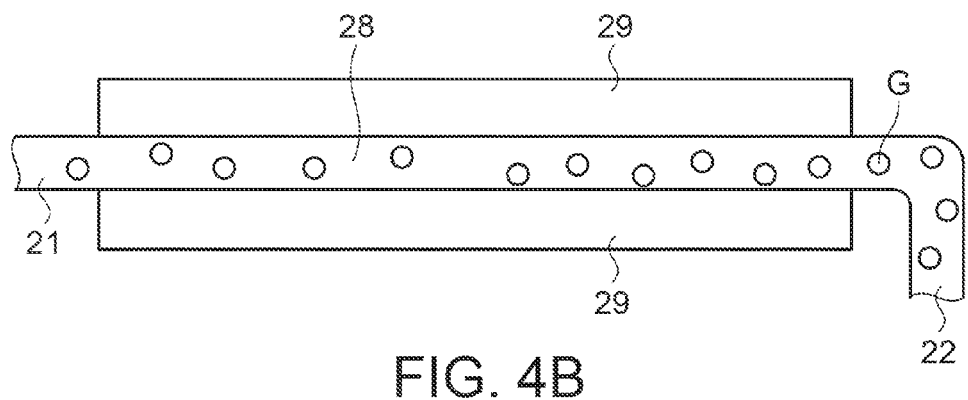

As shown in FIGS. 4A and 4B, in the second embodiment the meandering section 28 is disposed between the head mount section 26 and the discharge section 22 of the flow section 21. The meandering section 28 is made of, for example, transparent heat-resistant glass, and is formed to have a tubular shape. Thus, by changing the flow velocity of the second solution L2 and the gel G flowing through the meandering section 28, the gel G is made to snake through the inside the tubular shape of the meandering section 28. Thus, the gel G is made to collide with each other or the gel G and the inside of the tubular shape of the meandering section 28 are made to collide with each other inside the meandering section 28.

Figure 5:
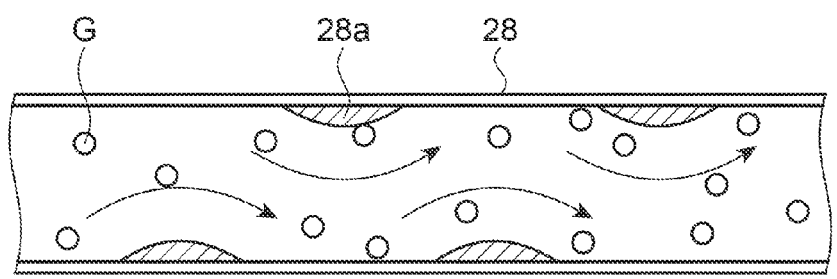
FIG. 5 is a schematic cross-sectional view showing details of the meandering section of the gel manufacturing apparatus according to the second embodiment.

Further, as shown in FIG. 5, it is also possible to form projections 28a inside the tubular shape of the meandering section 28, thus, turbulent flow is caused in the second solution L2 and the gel G flowing through the inside of the tubular shape of the meandering section 28. Further, the gel G is made to collide with the projections 28a using the turbulent flow.

The warming section 29 is disposed so as to sandwich the meandering section 28. The warming section 29 is, for example, a hot plate provided with an electrically-heated wire, or a heater. Using the warming section 29, the flow section 21 and the second solution L2 and the gel G flowing through the flow section 21 are warmed at a temperature no higher than 60° C. The warming section 29 can be disposed so as to wrap the meandering section 28 by being wound around the meandering section 28.

Therefore, according to the present embodiment, the advantages substantially the same as those of the embodiment described above are obtained, the flow velocity of the second solution L2 and the gel G is changed by snaking the second solution L2 and the gel G inside the tubular shape of the meandering section 28 using the meandering section 28. Further, by making the gel G collide with the projections 28a, the flow velocity of the second solution L2 and the gel G is changed.

As described above, the turbulent flow is caused in the second solution L2 and the gel G flowing through the inside of the tubular shape of the meandering section 28. For example, even in the case in which the gel G has a rough surface or a provided with a projection, and does not have a spherical shape, the gel G can be made closer to the spherical shape by making the gel G collide with each other, or making the gel G and the inside of the tubular shape of the meandering section 28 collide with each other, or making the gel G and the projections 28a collide with each other using the turbulent flow. Alternatively, even in the case in which a plurality of gels G flows from the flow section 21 in a state of being stuck with each other to form a string, the gels G are separated into a plurality of individual gels G in the meandering section 28, and then due to the collision described above, each of the gels G is made to have a spherical shape.

Further, by warming the gel G at a temperature higher than the room temperature and no higher than 60° C., the gel G can be cured in a shorter period of time.

Third Embodiment

A third embodiment of the invention will hereinafter be explained with reference to FIG. 6.

In the gel manufacturing apparatus 10 according to the third embodiment, the constituents identical to those of the first or the second embodiment shown in FIGS. 1 through 5 are denoted by the same reference numerals, and the explanations of the constituents will be omitted.

The gel manufacturing apparatus 10 according to the third embodiment is different from the gel manufacturing apparatus 10 according to the first or the second embodiment in that ultrasonic wave generation sections 33a, 33b are disposed between the head mount section 26 and the discharge section 22 of the flow section 21.

Figure 6:
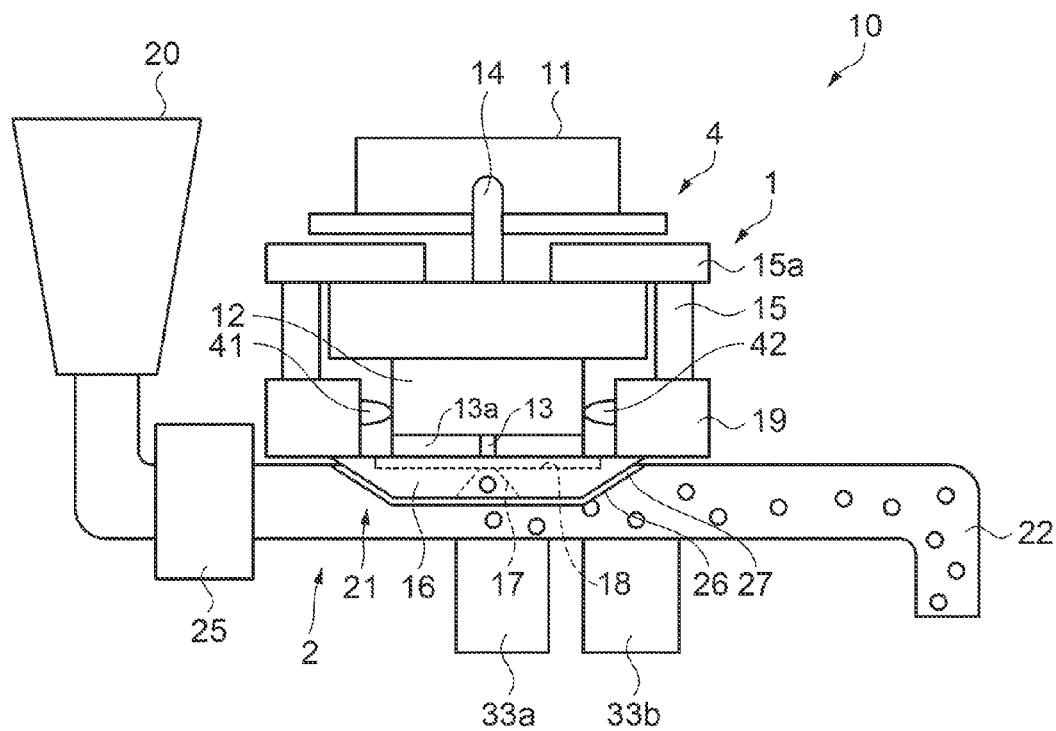
FIG. 6 is a schematic side view showing a gel manufacturing apparatus according to a third embodiment.

As shown in FIG. 6, the ultrasonic wave generation sections 33a, 33b apply ultrasonic waves different from each other to the second solution L2 and the gel G flowing therethrough. On the one hand, a low frequency wave of about 20 kHz is generated from the ultrasonic wave generation section 33a. On the other hand, a high frequency wave of about several MHz is generated from the ultrasonic wave generation section 33b.

According to the above configuration, by applying the low frequency wave of about 20 kHz to the second solution L2 and the gel G flowing therethrough, cavitation (bubbles) is generated. Thus, it is prevented that the gels G thus generated are stuck with each other or linked with each other to form a string.

Further, by applying the high frequency wave of several MHz to the second solution L2 and the gel G flowing therethrough, the molecules themselves of the second solution L2 are vibrated. Thus, it is prevented that the gels G thus generated are stuck with each other or linked with each other to form a string, and at the same time, it functions to make the gel G have a spherical shape.

Modified Examples

A configuration of housing the gel manufacturing apparatus 10 in a microwave generator such as a microwave oven can also be adopted.

According to this configuration, since the first solution L1 is ejected while vibrating the first solution L1 and the second solution L2 with the microwave, and the solutions are continuously vibrated after the ejection, it is prevented that the gels G thus generated are stuck with each other or linked with each other to form a string.

Fourth Embodiment

A fourth embodiment of the invention will hereinafter be explained with reference to FIGS. 7A and 7B.

In the gel manufacturing apparatus 10 according to the fourth embodiment, the constituents identical to those of the first through the third embodiments shown in FIGS. 1 through 6 are denoted by the same reference numerals, and the explanations of the constituents will be omitted.

The gel manufacturing apparatus 10 according to the fourth embodiment is different from the gel manufacturing apparatus 10 according to the first through the third embodiments in that there are disposed two flow sections 21.

Figure 7A:
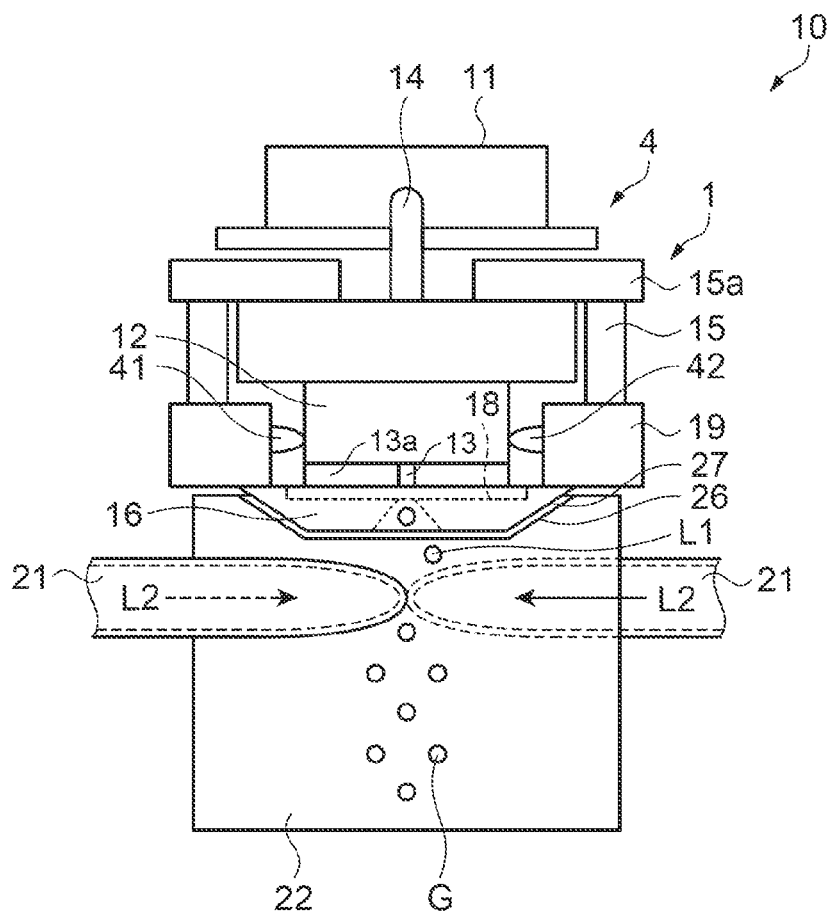
FIGS. 7A and 7B are schematic configuration diagrams showing a gel manufacturing apparatus according to a fourth embodiment.
Figure 7B:
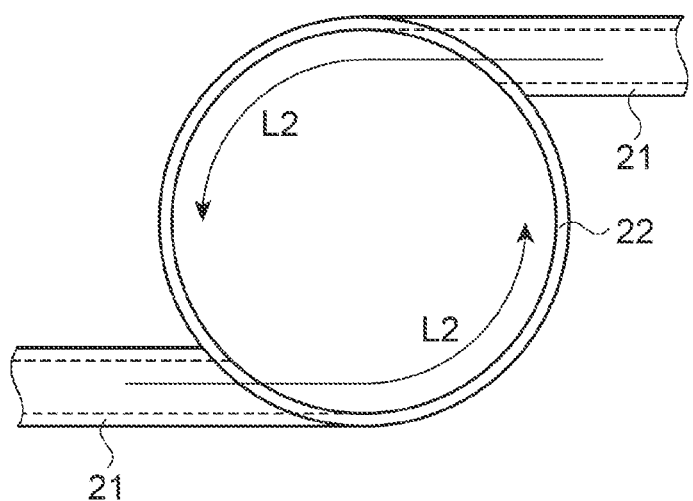

As shown in FIGS. 7A and 7B, the flow sections 21 are disposed in a direction perpendicular to the direction in which the first solution L1 is ejected from the nozzle 13 of the inkjet head 12. Further, the flow sections 21 are disposed at the positions shifted from the center of the discharge section 22 having a tubular shape. Further, it is arranged that the flow directions of the second solution L2 from the respective flow sections 21 are opposite to each other on the both sides across the center of the tubular shaped discharge section 22, namely one side and the other side. It is arranged that the second solution L2 flowing from the respective two flow sections 21 into the inside of the tubular shape of the discharge section 22 flows or rotates in the same direction inside the tubular shape of the discharge section 22 taking the center of the tubular shaped discharge section 22 as the flow center. Here, the two flow sections 21 can make the second solution L2 flow respectively from the separate second reservoirs 20, but this is not a limitation, and it is also possible to make the second solution L2 flow from the single second reservoir 20 to the two flow sections 21 separately. Further, the number of flow sections 21 is not limited to two, but can be one, or more than two.

Thus, the second solution L2 rotationally flows around the center of the tubular shaped discharge section 22 of the direction in which the first solution is ejected from the nozzle 13 to generate a swirl flow. As described above, since the second solution L2 is prevented from resting or being accumulated, and made to flow, it is possible to avoid the problems that the second solution L2 is contaminated or that living microbes are developed in the second solution L2.

Fifth Embodiment

Figure 8:
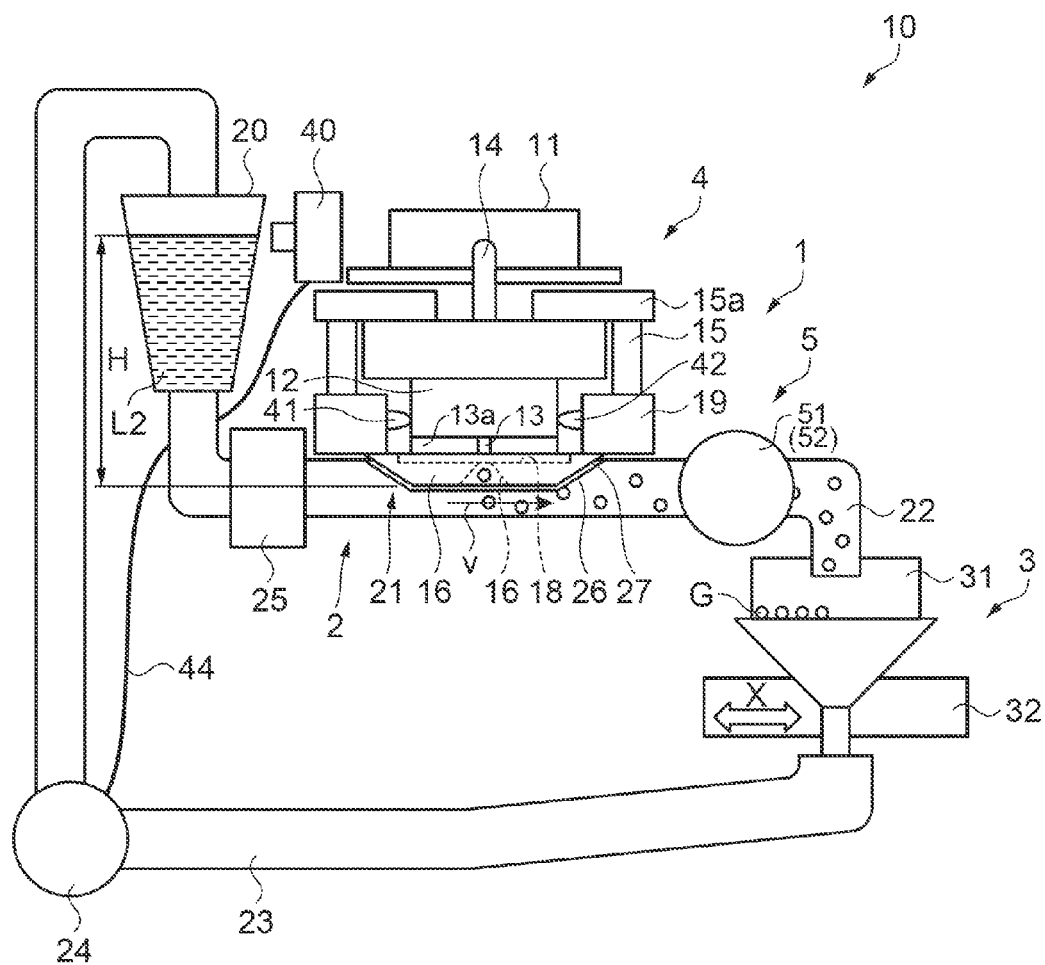
FIG. 8 is a schematic side view showing a gel manufacturing apparatus according to a fifth embodiment.

A fifth embodiment of the invention will hereinafter be explained with reference to FIG. 8.

In the gel manufacturing apparatus 10 according to the fifth embodiment, the constituents identical to those of the first through the fourth embodiments shown in FIGS. 1 through 7B are denoted by the same reference numerals, and the explanations of the constituents will be omitted.

The gel manufacturing apparatus 10 according to the fifth embodiment is different from the gel manufacturing apparatus 10 according to the first through the fourth embodiments in that the position of the liquid level of the second solution L2 contained in the second reservoir 20 is detected by a fluid level sensor 40, and the flow velocity of the second solution L2 flowing through the flow section 21 is controlled.

Assuming that the height difference between the position of the liquid level of the second solution L2 contained in the second reservoir 20 detected by the fluid level sensor 40 and the second solution L2 flowing immediately beneath the nozzle 13 is H, and the flow velocity of the second solution L2 flowing immediately beneath the nozzle 13 of the inkjet head 12 is V, the formula (1) below is obtained. In this case, g denotes the gravity acceleration.

$$V=\sqrt{2gH} \quad (1)$$

If the position of the liquid level detected by the fluid level sensor 40 is lower than the height difference H, the drive signal from the fluid level sensor 40 is transmitted to the pump 24 via the signal line 44 to drive the pump 24, thereby supplying the second solution L2 from the solution circulation section 23 to the inside of the second reservoir 20. Further, if the position of the liquid level detected by the fluid level sensor 40 is higher than the height difference H, the stop signal from the fluid level sensor 40 is transmitted to the pump 24 via the signal line 44 to stop to drive the pump 24, thereby stopping to supply the second solution L2 from the solution circulation section 23 to the inside of the second reservoir 20. In such a manner as described above, the flow velocity V of the second solution L2 flowing immediately beneath the nozzle 13 of the inkjet head 12 is determined.

Thus, in the present embodiment, in the case in which the diameter of the gel G is 100 μm and the ejection frequency is 10 Hz for example, the flow velocity V is set to be 1 mm/s or higher.

It should be noted that modifications, improvements, and so on within the range where at least a part of problems described above can be solved can be included in the embodiment described above.

For example, although in the embodiment described above, it is assumed that the solution circulation section 23 collects the second solution L2 flowing through the discharge section 22, and circulates it to the second reservoir 20 with the pump 24, the invention is not limited thereto, but it is also possible to arrange that the solution circulation section 23 collects the second solution L2 in the second reservoir 20, and circulates it to the flow section 21 with the pump 24.

Further, although in the embodiment described above, it is assumed that the second solution L2 flowing through the discharge section 22 and the solution circulation section 23 is collected, and then circulated to the second reservoir 20 with the pump 24, the invention is not limited thereto, but it is also possible to arrange that the second solution L2 flowing through the discharge section 22 and the solution circulation section 23 is collected to a collection reservoir, and then, after filtrating the second solution L2 collected in the collection reservoir, the second solution L2 is contained in the second reservoir 20.

Further, although in is assumed that the gel manufacturing apparatus 10 is made of transparent acrylic resin, or transparent or translucent polypropylene and so on, the invention is not limited thereto, but it is also possible to arrange that an obscure material can also be adopted, and the gel manufacturing apparatus 10 can be made of glass or metal providing the material does not alter nor react with the first solution, the second solution, and the gel thus generated.

The entire disclosure of Japanese Patent Application No. 2009-167542, filed Jul. 16, 2009 is expressly incorporated by reference herein.

What is claimed is:

1. A gel manufacturing apparatus adapted to generate gel by making a first solution and a second solution react with each other, comprising:
a flow mechanism adapted to make the second solution flow;
an ejection mechanism having a nozzle plate provided with a nozzle adapted to eject the first solution to the second solution made to flow using a droplet ejection method; and
a gap plate provided with a through hole communicated with the nozzle,
wherein the gap plate is disposed between the flow mechanism and the ejection mechanism.

2. The gel manufacturing apparatus according to claim 1, wherein
a groove is formed on a surface of the gap plate, opposed to the ejection mechanism, the groove being communicated with the through hole.

3. The gel manufacturing apparatus according to claim 1, wherein
the through hole on the flow mechanism side has a round shape.

4. The gel manufacturing apparatus according to claim 1, wherein
a diameter of the through hole on the flow mechanism side is larger than the diameter of the through hole on the ejection mechanism side.

5. The gel manufacturing apparatus according to claim 1, wherein
the flow mechanism further includes a meandering section adapted to snake the gel and the second solution.

6. The gel manufacturing apparatus according to claim 5, wherein
the meandering section has a projection on an inside wall.

7. The gel manufacturing apparatus according to claim 5, further comprising:
a warming section adapted to warm the meandering section.

8. The gel manufacturing apparatus according to claim 1, further comprising:
a first ultrasonic wave generation section adapted to apply an ultrasonic wave in a first frequency band to the second solution and the gel; and
a second ultrasonic wave generation section adapted to apply an ultrasonic wave in a second frequency band higher than the first frequency band to the second solution and the gel.

9. The gel manufacturing apparatus according to claim 1, further comprising:
a second flow mechanism adapted to make the second solution flow in a direction opposite to the direction in which the flow mechanism makes the second solution flow.

10. The gel manufacturing apparatus according to claim 1, further comprising:
a reservoir adapted to contain the second solution;
a sensor adapted to detect a liquid level position of the second solution contained in the reservoir; and
a control section adapted to control a flow velocity of the second solution based on the liquid level position the sensor detects.

11. The gel manufacturing apparatus according to claim 1, wherein
a thickness of the gap plate in a direction in which the first solution is ejected is in a range no smaller than 0.1 mm and no larger than 10 mm.

12. The gel manufacturing apparatus according to claim 1, wherein
the first solution is a sodium alginate water solution.

13. The gel manufacturing apparatus according to claim 1, wherein
the second solution is a calcium chloride water solution.

* * * * *